United States Patent
Sullivan et al.

(10) Patent No.: US 10,172,606 B2
(45) Date of Patent: Jan. 8, 2019

(54) TENSIONABLE KNOTLESS ANCHORS AND METHODS OF TISSUE REPAIR

(71) Applicant: Arthrex, Inc., Naples, FL (US)

(72) Inventors: Derek C. Sullivan, Bonita Springs, FL (US); William C. Benavitz, Naples, FL (US); Thomas Dooney, Jr., Naples, FL (US); Lee D. Kaplan, Miami, FL (US); James P. Bradley, Pittsburgh, PA (US)

(73) Assignee: Arthrex, Inc., Naples, FL (US)

( * ) Notice: Subject to any disclaimer, the term of this patent is extended or adjusted under 35 U.S.C. 154(b) by 259 days.

(21) Appl. No.: 15/004,154

(22) Filed: Jan. 22, 2016

(65) Prior Publication Data

US 2017/0209135 A1 Jul. 27, 2017

(51) Int. Cl.
 *A61B 17/04* (2006.01)
 *A61F 2/08* (2006.01)

(52) U.S. Cl.
 CPC ...... *A61B 17/0401* (2013.01); *A61B 17/0483* (2013.01); *A61F 2/0811* (2013.01); *A61B 2017/0403* (2013.01); *A61B 2017/044* (2013.01); *A61B 2017/0409* (2013.01); *A61B 2017/0414* (2013.01); *A61B 2017/0445* (2013.01); *A61F 2002/0888* (2013.01)

(58) Field of Classification Search
 CPC ........ A61B 17/0401; A61B 2017/0403; A61B 2017/0445; A61B 2017/0464; A61B 2017/0404; A61B 2017/0414
 See application file for complete search history.

(56) References Cited

U.S. PATENT DOCUMENTS

| | | | |
|---|---|---|---|
| 6,716,234 B2 | 4/2004 | Grafton et al. | |
| 7,329,272 B2 | 2/2008 | Burkhart et al. | |
| 7,713,285 B1 * | 5/2010 | Stone | A61B 17/0401 606/232 |
| 7,892,256 B2 | 2/2011 | Grafton et al. | |
| 8,012,174 B2 | 9/2011 | ElAttrache et al. | |
| 9,005,246 B2 | 4/2015 | Burkhart et al. | |
| 9,107,653 B2 | 8/2015 | Sullivan | |
| 2009/0248068 A1 * | 10/2009 | Lombardo | A61B 17/0401 606/232 |
| 2009/0312794 A1 * | 12/2009 | Nason | A61B 17/0401 606/232 |
| 2010/0160962 A1 * | 6/2010 | Dreyfuss | A61B 17/0401 606/228 |
| 2010/0179573 A1 * | 7/2010 | Levinsohn | A61B 17/0401 606/145 |
| 2011/0118762 A1 * | 5/2011 | Dooney, Jr. | A61B 17/0401 606/148 |
| 2012/0041484 A1 * | 2/2012 | Briganti | A61B 17/0401 606/232 |

(Continued)

*Primary Examiner* — Amy R Weisberg
(74) *Attorney, Agent, or Firm* — Blank Rome LLP

(57) ABSTRACT

Surgical devices and methods of surgical repairs using the devices are disclosed. The device and methods aid in surgical repairs by allowing for quick and reproducible repairs to be made. A tensionable knotless fixation device is provided with a tensioning construct (formed of a tensioning strand, a tensionable, adjustable, knotless, self-cinching loop, and a splice adjacent the loop) pre-loaded onto a fixation device. A flexible material (for example, suture or suture tape) may be attached to a fixation device. A flexible material may be threaded through an eyelet of a fixation device.

21 Claims, 18 Drawing Sheets

(56) References Cited

U.S. PATENT DOCUMENTS

| | | | |
|---|---|---|---|
| 2013/0023928 A1* | 1/2013 | Dreyfuss | A61B 17/0401 606/228 |
| 2013/0023929 A1* | 1/2013 | Sullivan | A61B 17/0401 606/232 |
| 2013/0096611 A1* | 4/2013 | Sullivan | A61B 17/0485 606/232 |
| 2013/0165972 A1 | 6/2013 | Sullivan | |
| 2013/0296936 A1 | 11/2013 | Burkhart | |
| 2013/0345750 A1* | 12/2013 | Sullivan | A61B 17/0401 606/232 |
| 2015/0297211 A1* | 10/2015 | Sullivan | A61B 17/0401 606/232 |
| 2017/0209135 A1* | 7/2017 | Sullivan | A61B 17/0401 |
| 2017/0209139 A1* | 7/2017 | Burkhart | A61B 17/0401 |

\* cited by examiner

TENSIONABLE KNOTLESS ANCHORS AND METHODS OF TISSUE REPAIR

BACKGROUND

The present disclosure relates to surgical devices and methods and, more particularly, to surgical devices and methods for use in tissue repair.

SUMMARY

Surgical assemblies, systems and techniques for knotless soft tissue repair and fixation, such as fixation of soft tissue (ligament, tendon, graft, etc.) to bone, are disclosed. Surgical assemblies comprise tensionable knotless fixation devices that are inserted into bone. A tensionable knotless fixation device is provided with a tensioning construct (formed of a tensioning strand, a tensionable, adjustable, knotless, self-cinching loop, and a splice adjacent the loop) pre-loaded onto a fixation device. A flexible material (for example, suture or suture tape) may be attached to a fixation device. A flexible material may be threaded through an eyelet of a fixation device.

Methods of soft tissue repair which do not require tying of knots and allow adjustment of both tension of suture and location of tissue with respect to bone are also disclosed.

DETAILED DESCRIPTION

Figure 1:
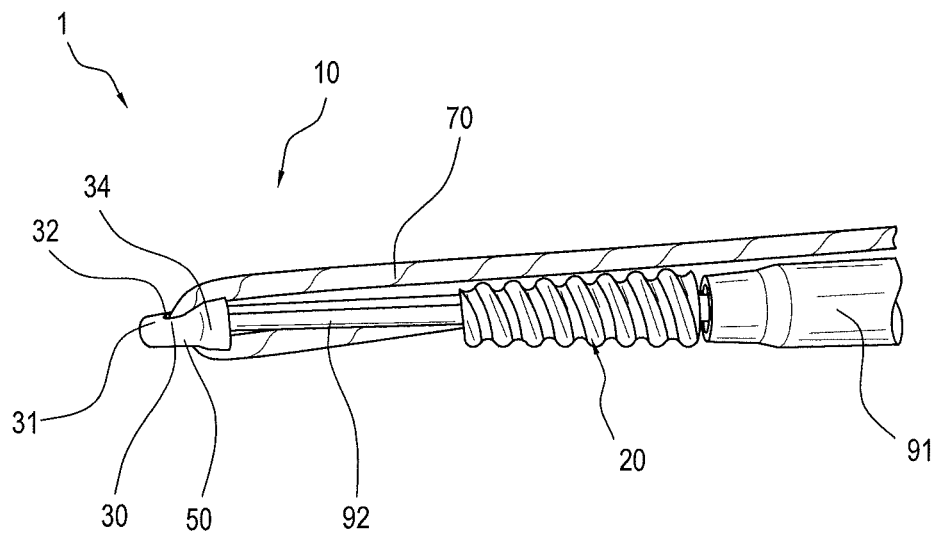
FIGS. 1 and 2 illustrate an exemplary embodiment of a fixation device loaded onto a driver.

Surgical assemblies, systems and techniques for knotless soft tissue repair and fixation, such as fixation of soft tissue (ligament, tendon, graft, etc.) to bone, are disclosed. Surgical assemblies comprise tensionable knotless fixation devices that are inserted into bone. Tensionable knotless fixation devices are provided with a tensioning construct (formed of a tensioning strand, a tensionable, adjustable, knotless self-cinching loop, and a splice adjacent the loop) pre-loaded onto the fixation device. A flexible material (for example, suture or suture tape) may be attached to the fixation device, for example, by being threaded through an eyelet of the fixation device.

As detailed below, the surgical assemblies and devices disclosed allow for knotless fixation of tissue using an eyelet suture of a fixation device (for example, a suture anchor with an eyelet or a SwiveLock® anchor). A mechanism inside the suture eyelet is similar to the knotless tensionable construct of the SutureTak®, except that there is no post or similar device within the anchor body to allow suture to wrap around. The knotless tensionable construct passes the anchor body of modified SwiveLock® anchors. In this manner, the surgical assemblies and devices detailed below combine two technologies to provide a strong knotless repair, as well as a backup knotless repair separate from a first repair.

Methods of soft tissue repair which do not require tying of knots and allow adjustment of both the tension of the suture and the location of the tissue with respect to the bone are also disclosed.

A surgical assembly can include (i) a fixation device; (ii) a tensionable construct pre-loaded on the fixation device; and (iii) a flexible material (for example, suture or suture tape) attached to the fixation device. A flexible material may be also pre-loaded on the fixation device, and may be releasably attached to the fixation device, or securely fixed to it. The fixation device can include an anchor body insertable over an anchor tip, the anchor tip including a shaft attached to an anchor tip body, the anchor tip body being provided with first and second apertures or openings (for example, an eyelet oriented in a first direction and a through-hole or passage oriented in a second direction, which may be different from the first direction). A tensionable construct may be pre-loaded on the fixation device. The tensionable construct may consist of a flexible strand with a knot and a free end, a splice and an adjustable, tensionable, self-cinching, knotless, closed loop having an adjustable perimeter, located adjacent the splice. The tensionable construct passes through the anchor tip and extends through at least a portion of the anchor body of the fixation device.

The fixation device may be a SwiveLock® anchor as disclosed and described, for example, in U.S. Pat. No. 8,012,174 issued Sep. 6, 2011, U.S. Pat. No. 9,005,246 issued Apr. 14, 2015, and U.S. 2013/0296936 published Nov. 7, 2013, the disclosures of all of which are fully incorporated by reference in their entirety herein, with or without a modified eyelet in the anchor tip, and as detailed below.

The flexible material (suture construct) can be any suture strand or suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. However, the fixation devices detailed below can be used with any type of flexible material or suture known in the art.

The tensionable construct may use a mechanism similar to that of knotless SutureTak® but provides variations and improvements in the design of the tensioning construct. Details of the formation of an exemplary tensioning construct employed in the embodiments of the present invention detailed below are set forth in U.S. Pat. No. 9,107,653 issued Aug. 18, 2015; U.S. 2013/0165972, entitled "Tensionable Knotless Anchor Systems and Methods of Tissue Repair;" and U.S. 2013/0345750, entitled "Tensionable Knotless Labral Anchor and Methods of Tissue Repair," the disclosures of all of which are incorporated by reference in their entirety herein.

The tensionable construct may be formed of a flexible strand or flexible material that is easily spliced through itself to form a splice and a knotless, self-cinching, adjustable, closed loop with an adjustable perimeter. The flexible strand or material may be made of any known suture material, such as ultrahigh molecular weight poly ethylene (UHMWPE) or FiberWire® suture (disclosed in U.S. Pat. No. 6,716,234 the disclosure of which is herein incorporated by reference in its entirety), and can be braided or multi-filament. For example, the suture can be UHWMPE suture without a core to permit ease of splicing.

FIG. 1 illustrates an exemplary embodiment of a fixation device 10 (tensionable knotless fixation device 10) seated on a driver 91. Tensionable knotless fixation device 10 comprises an anchor body 20 and an anchor tip 30, the anchor body 20 being insertable over the anchor tip 30. A tensionable construct 50 (also referred to as "tensioning construct 50") and a flexible material 70 are pre-loaded on the fixation device 10 to form surgical assembly 1. Tensionable knotless fixation device 10 is seated on driver 91. Driver 91 has a thin cannulated rod 92, where anchor tip 30 is seated at the proximal end 94 of the thin cannulated rod 92. Anchor body 20 is cannulated and is fully seated around thin cannulated rod 92.

Tensionable construct 50 is pre-loaded onto the fixation device 10, and extends through at least a portion of the fixation device. Flexible material 70 may be also pre-loaded onto the fixation device 10.

Anchor tip 30 includes anchor tip body 31 attached to a cannulated shaft 36 (not shown in FIG. 1), wherein the cannulated shaft 36 is at least partially disposed within thin cannulated rod 92 of driver 91. Anchor tip body 31 is also provided with first and second through-holes, openings, or passages 32, 34. In an exemplary embodiment, one of the first and second through-holes, openings, or passages is an eyelet 32 having a first orientation relative to a longitudinal axis of the anchor tip, and the other of the first and second-through holes, openings, or passages is a flexible material hole or passage 34 (a transverse opening 34) having a second orientation relative to a longitudinal axis of the anchor tip. In an exemplary embodiment, the first orientation is different from the second orientation. In another exemplary embodiment, the first orientation is about perpendicular to the second orientation. Eyelet 32 accommodates and houses tensionable construct 50. Hole, opening, or passage 34 accommodates and houses flexible material 70.

Figure 2:
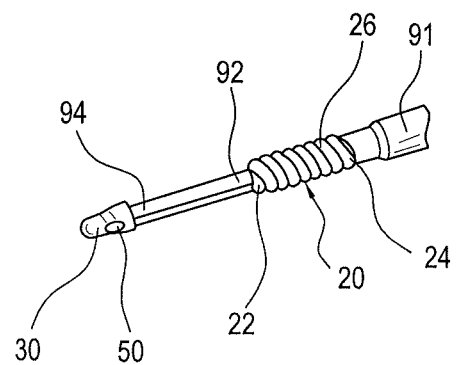

FIG. 2 illustrates another view of tensionable knotless fixation device 10 pre-loaded with tensionable construct 50 but without flexible material 70.

During installation of fixation device 10, anchor body 20 is assembled onto the operational end of the driver 91. Anchor tip 30 is threaded or otherwise attached onto the tip of thin cannulated rod 92. Anchor tip 30 is then placed within a prepared bone hole or tunnel until anchor tip 30 reaches the bottom of the bone hole or tunnel, or reaches the desired depth. At this point, anchor body 20 is still outside of the bone hole or tunnel. Anchor body 20 is then reduced down thin cannulated rod 92 (advanced down the cannulated rod to be insertable over the anchor tip 30) by holding a thumb pad (not pictured) as the inserter handle (not pictured) of the driver 91 is turned clockwise. When anchor body 20 is fully seated, cannulated shaft 36 of anchor tip 30 is fully engaged by cannulated anchor body 20, creating a stable swivel construct of the fixation device 10 wherein anchor tip 30 is rotatably secured to anchor body 20.

In an exemplary embodiment, anchor body 20 is cannulated and has a proximal end 22 and a distal end 24, wherein proximal end 22 is the end closest to anchor tip 30. The exterior 26 of anchor body 20 can be threaded, for example like a screw, or can be any suitable means for securing in a bone hole or tunnel, for example, in the form of circumferential ridges extending radially. The exterior 26 of anchor body 20 is responsible for both securing fixation device 10 in the bone hole or tunnel, as well as securing, by friction or interference fit, suture construct 70 against the bone wall and exterior 26 of anchor body 20.

Anchor body 20 (in the form of a cannulated fixation device 20 or cannulated screw 20) may be pre-loaded onto the shaft of the driver. The anchor tip 30 (implant 30) is designed to be releasably attached (by a snap fit, for example) to a distal end of the driver and to swivel relative to the anchor body 20 (cannulated fixation device 20). The anchor tip (implant) with attached suture is anchored into bone by rotating the driver to rotate and advance the anchor body 20 (cannulated fixation device 20) while keeping the anchor tip 30 (implant 30) stationary, thereby securing the suture and providing tissue fixation without tying knots in the suture. The driver with the cannulated rod (passing slidably and rotatably through a cannulated driver assembly of the driver) has a tip adapted to accept the anchor tip 30 (implant 30), to allow the anchor tip 30 to be loaded onto the rod and be fully seated on an end of the shaft of the driver.

The anchor tip 30 (implant 30) is rotatably received within the anchor body 20 upon advancement of the anchor body 20 over a shaft of the anchor tip 30, the anchor tip 30 being configured to receive the tensionable construct and the flexible material. The anchor tip has a closed aperture or eyelet to receive the flexible material (suture or suture tape) to be attached to bone. The anchor tip 30 may be a metal tip and the anchor body 20 may have a cylindrical, screw-like configuration (for example, a cannulated interference screw).

Flexible material 70 can comprise any type of flexible material or suture known in the art, preferably suture tape such as Arthrex FiberTape®, or combination of suture and suture tape, among many others. Flexible material 70 can be configured to be pre-loaded or threaded through eyelet 32 of anchor tip 30. A first limb 72a and a second limb 72b pass outside of anchor body 20 and are secured against the bone wall and exterior 26 by friction or interference fit. In an exemplary embodiment, first limb 72a and second limb 72b can terminate into a single suture passing limb 74 to simplify passing each of limbs 72a and 72b through tissue. In this manner, both limbs 72a and 72b can be passed at the same time. After passing limb 74 is passed through tissue, it can be cut and removed, leaving first limb 72a and second limb 72b separated and passed through tissue.

In another embodiment, first limb 72a and second limb 72b do not terminate into a single passing limb, and are passed through tissue separately. In this embodiment, flexible material 70 may or may not be pre-loaded through eyelet 32 of anchor tip 30. In another embodiment, first limb 72a and second limb 72b do not terminate into a single suture passing limb, but both are loaded into a suture passer together and passed together.

Figure 3:
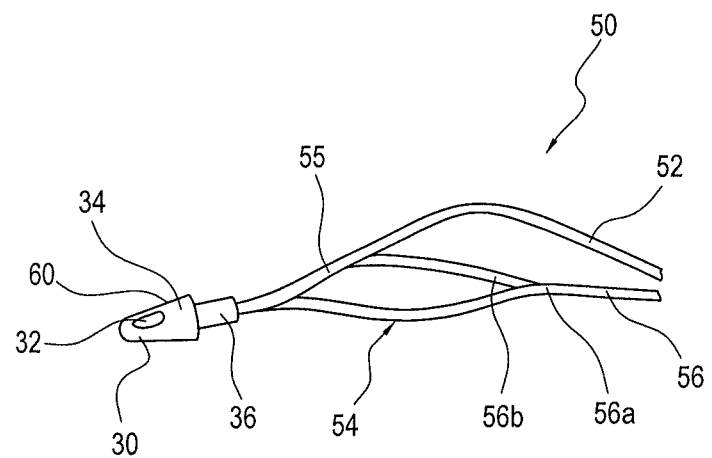
FIGS. 3 and 4 illustrate an exemplary embodiment of an anchor tip loaded with a tensioning construct.

FIG. 3 illustrates an exemplary embodiment of anchor tip 30 with tensionable construct 50 preloaded onto anchor tip 30. Tensionable construct 50 comprises a tensioning strand 52, a tensionable loop 54, a splice 55, and fixed loop strands 56a and 56b of stand 56 attached to loop 54. Fixed loop strands 56a and 56b pass through tensionable loop 54 and can terminate into a single loop strand 56. Loop strand 56 and tensioning strand 52 can then terminate into a single tensioning construct passing limb 58. In another embodiment, loop strands 56a and 56b do not terminate into a single loop strand 56, but instead terminate along with tensioning strand 52 into tensioning construct passing limb 58. In this embodiment, three limbs terminate into one limb at the same place. Tensioning construct passing limb 58 can be passed through tissue and then cut and removed. Loop strands 56a and 56b can then be discarded, leaving tensioning strand 52 and tensionable loop 54 passed through the tissue. Multiple tensionable loop strands may be provided attached to loop 54 (for example, passed through the loop 54). Loop 54 is a knotless, tensionable, adjustable, self-cinching loop having an adjustable perimeter.

Figure 4:
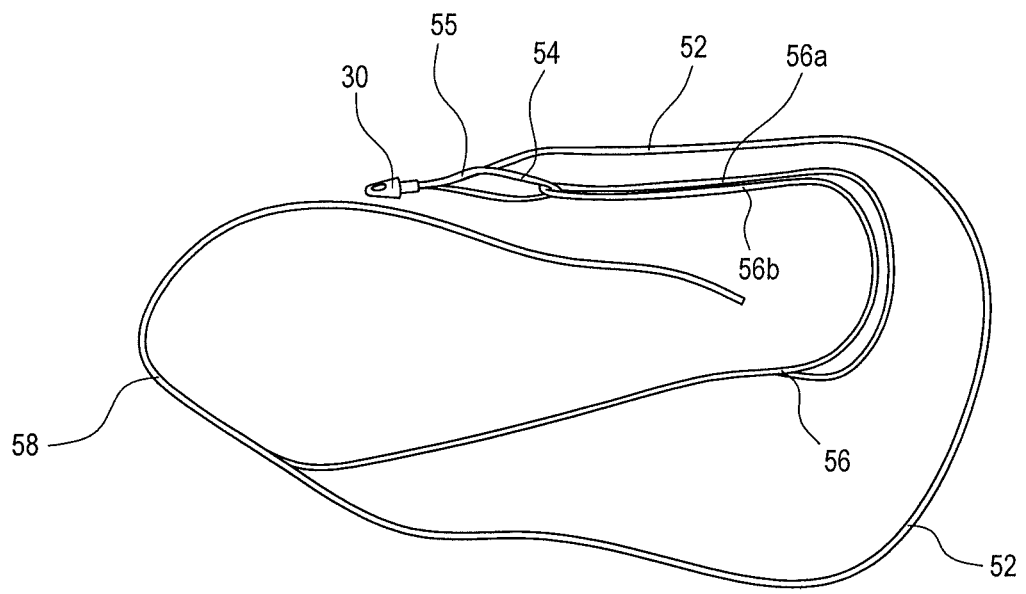
Figure 5:
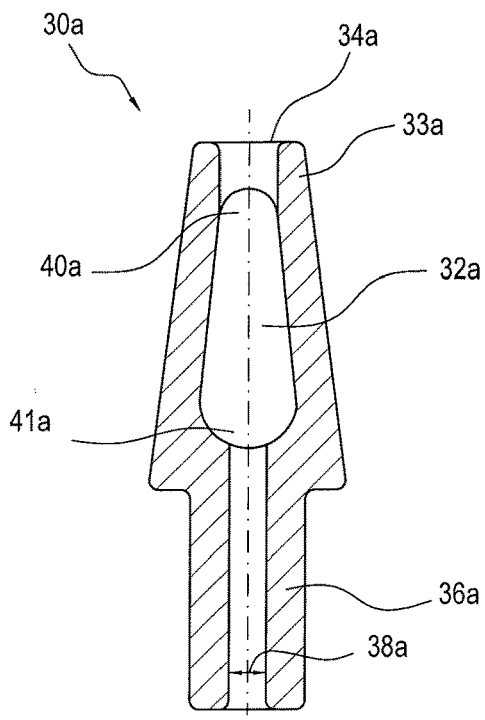
FIGS. 5-8 illustrate an exemplary embodiment of an anchor tip.
Figure 6:
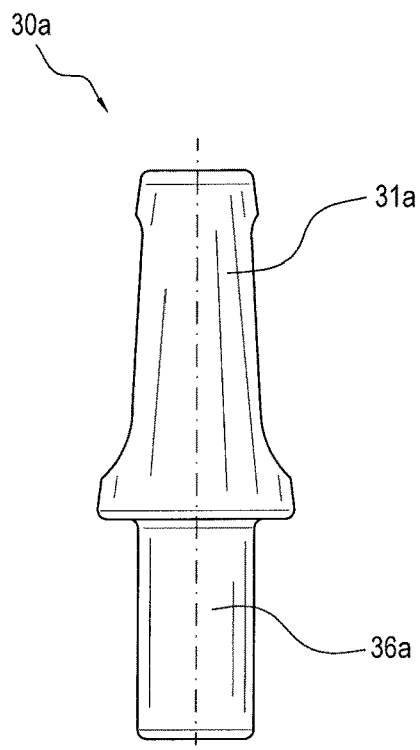
Figure 7:
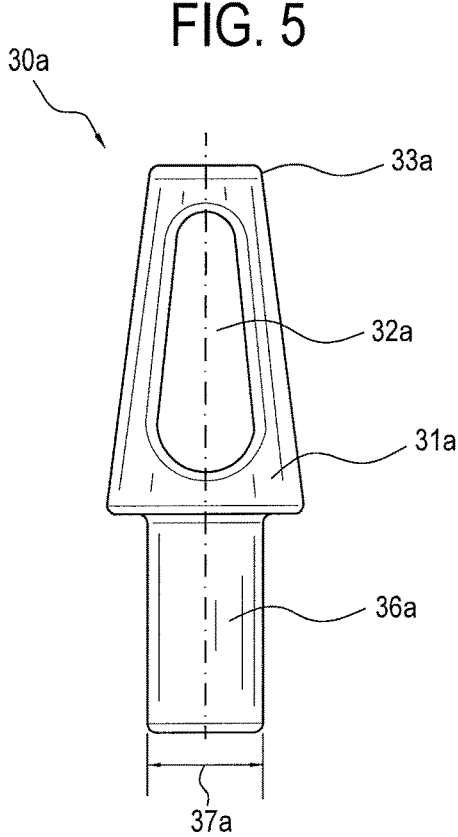
Figure 8:
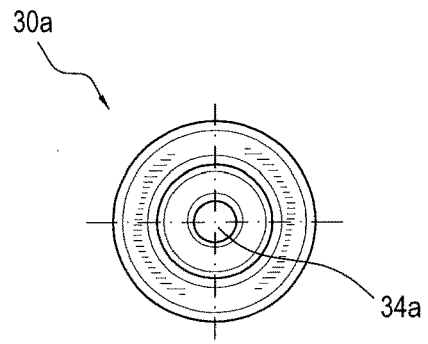

Tensionable construct 50 can be pre-loaded onto anchor tip 30 by tying static knot 60 on the outside of hole 34. Tensioning strand 52, tensionable loop 54, splice 55, and loop strands 56a and 56b pass through cannulated shaft 36 of anchor tip 30 and then through cannulated anchor body 20, exiting fixation device 10 at distal end 24 of anchor body 20. FIG. 4 illustrates loop strands 56a, 56b terminating into loop strand 56, and then loop strand 56 and tensioning strand 52 terminating into tensioning construct passing limb 58.

FIGS. 5-18 illustrate various exemplary embodiments 30a-30d of anchor tip 30.

FIGS. 5-8 illustrate exemplary embodiment 30a of anchor tip 30. Anchor tip 30a can include eyelet 32a, hole 34a, and cannulated shaft 36a. Hole 34a is positioned at the proximal tip of anchor tip 30a. Cannulated shaft 36a can have an outer width 37a and an inner width 38a, where inner width 38a represents how wide the hollow portion of cannulated shaft 36a is. In an exemplary embodiment, hole 34a can be wider than the inner width 38a. In another exemplary embodiment, hole 34a and inner width 38a can be approximately the same width. In another exemplary embodiment, hole 34a can be narrower than inner width 38a. Additionally, tip body 31a can be wider than outer width 37a of cannulated shaft 36a. Proximal end 33a of anchor tip 30a can be wider than, about as wide as, or narrower than, outer width 37a of cannulated shaft 36a. The size and shape of eyelet 32a can be any suitable size and shape. In the exemplary embodiment of FIGS. 5-8, eyelet 32a has two rounded ends, wherein first rounded end 40a, located near proximal end 33a of anchor tip 30a, is smaller than second rounded end 41a located near cannulated shaft 36a.

Figure 9:
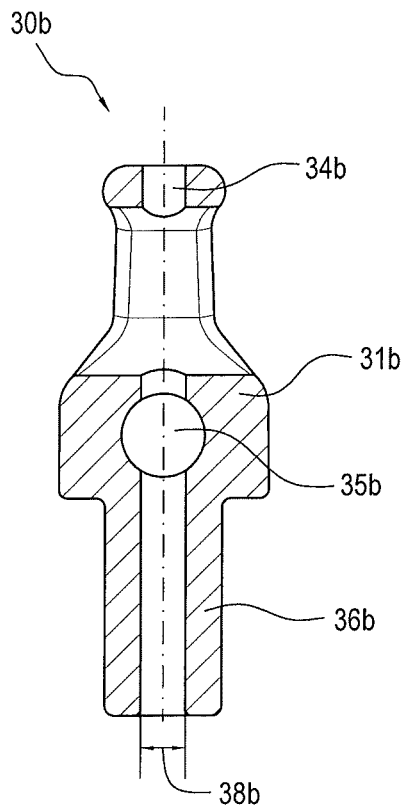
FIGS. 9-11 illustrate another exemplary embodiment of an anchor tip (a 3.5 mm round eyelet).
Figure 10:
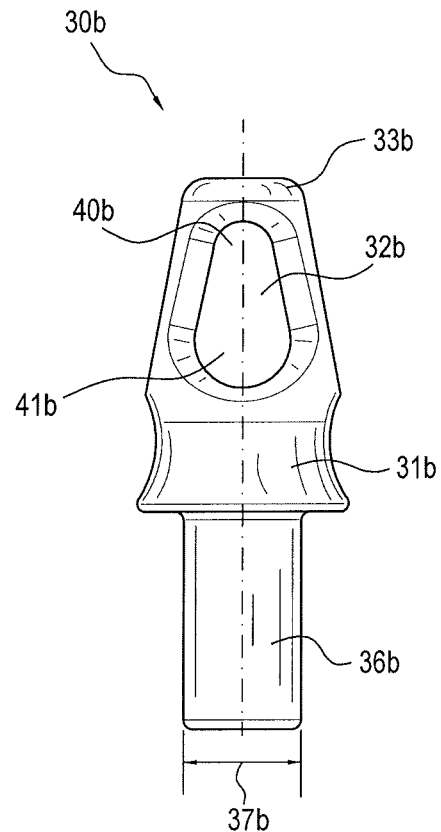
Figure 11:
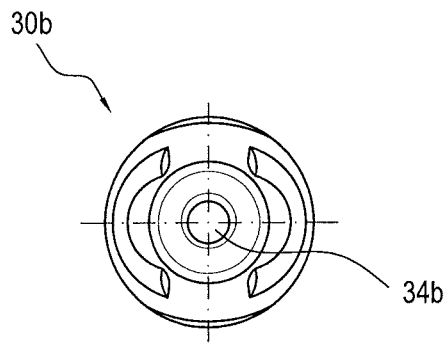

FIGS. 9-11 illustrate another exemplary embodiment 30b of anchor tip 30. Anchor tip 30b can include eyelet 32b, hole 34b, and cannulated shaft 36b. Hole 34b is positioned at positioned at the proximal tip of anchor tip 30b. Anchor tip 30b can further have a second hole 35b located on the side of anchor tip body 31b. Cannulated shaft 36b can have an outer width 37b and an inner width 38b, where inner width 38b represents how wide the hollow portion of cannulated shaft 36b is. In an exemplary embodiment, hole 34b can be wider than the inner width 38b. In another exemplary embodiment, hole 34b and inner width 38b can be approximately the same width. In another exemplary embodiment, hole 34b can be narrower than inner width 38b. Additionally, tip body 31b can be wider than outer width 37b of cannulated shaft 36b. Proximal end 33b of anchor tip 30b can be wider than, about as wide as, or narrower than outer width 37b of cannulated shaft 36b. The size and shape of eyelet 32b can be any suitable size and shape. In the exemplary embodiment of FIGS. 9-11, eyelet 32b has two rounded ends, wherein first rounded end 40b, located near proximal end 33b of anchor tip 30b, is smaller than second rounded end 41b located near cannulated shaft 36b.

Figure 12:
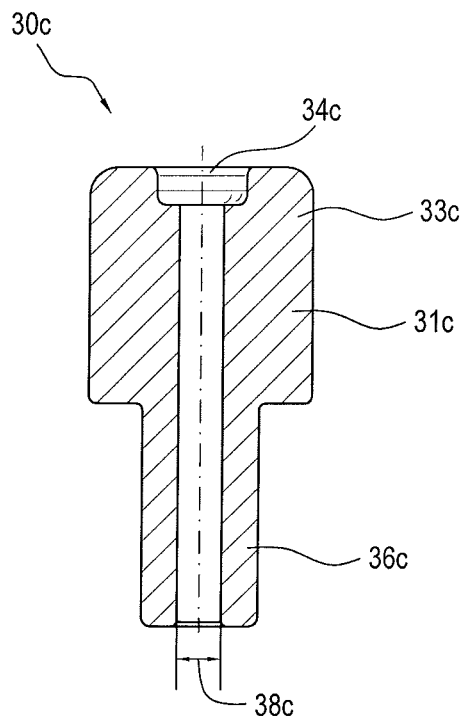
FIGS. 12-14 illustrate another exemplary embodiment of an anchor tip (a 4 mm round eyelet).
Figure 13:
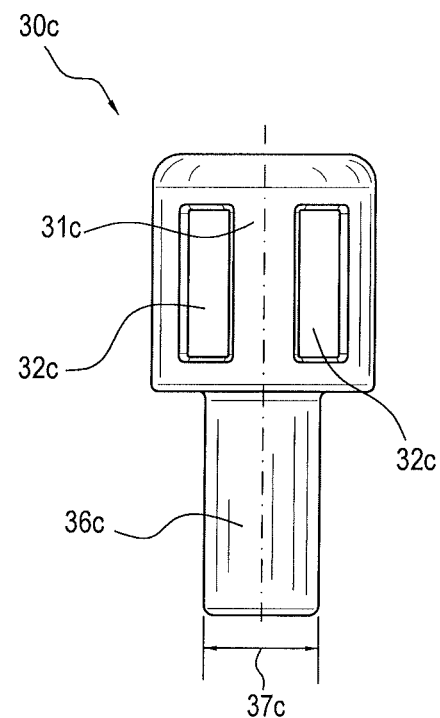
Figure 14:
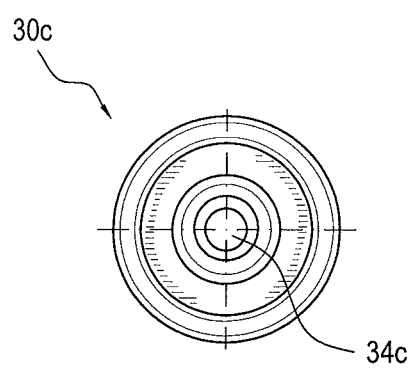
Figure 15:
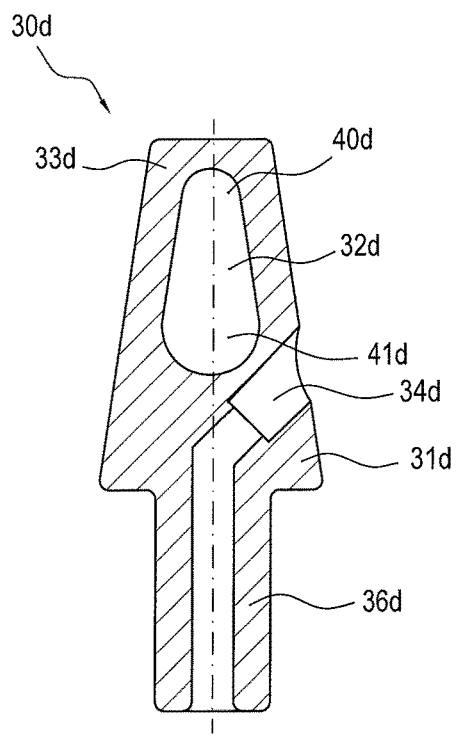
FIGS. 15-18 illustrate another exemplary embodiment of an anchor tip (an elongated open eyelet, curved).
Figure 16:
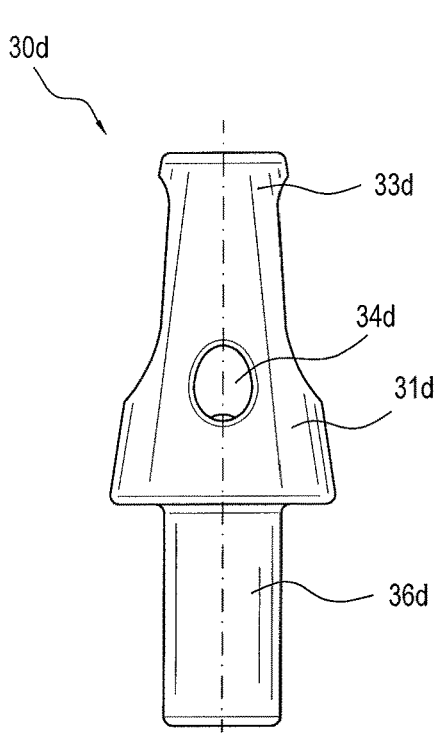
Figure 17:
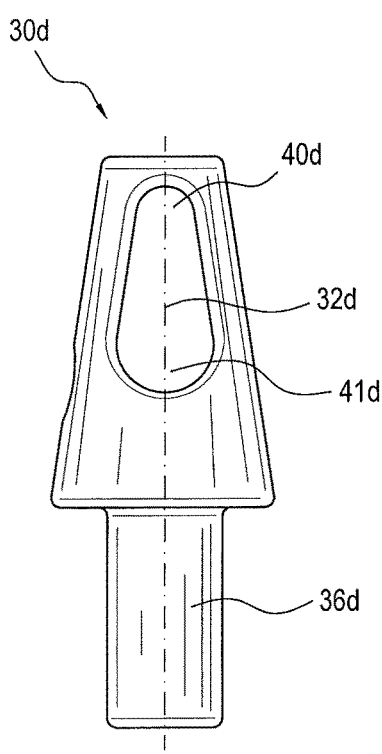
Figure 18:
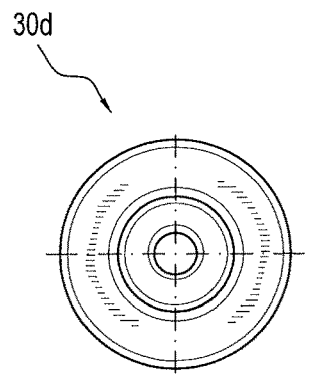
Figure 19A:
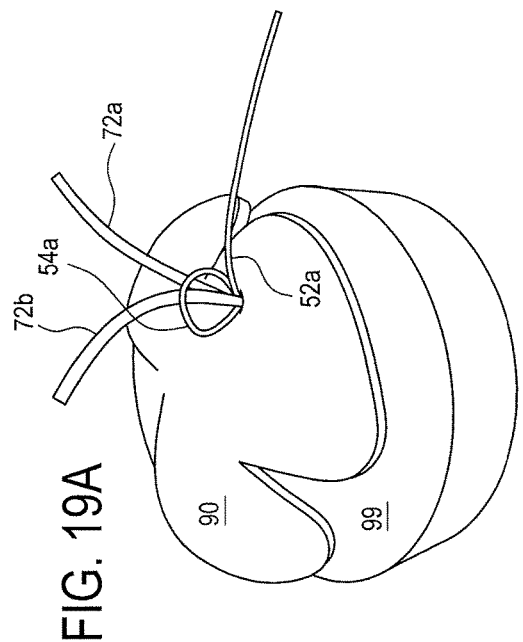
FIGS. 19A-D illustrate an exemplary embodiment of a surgical assembly.
Figure 19B:
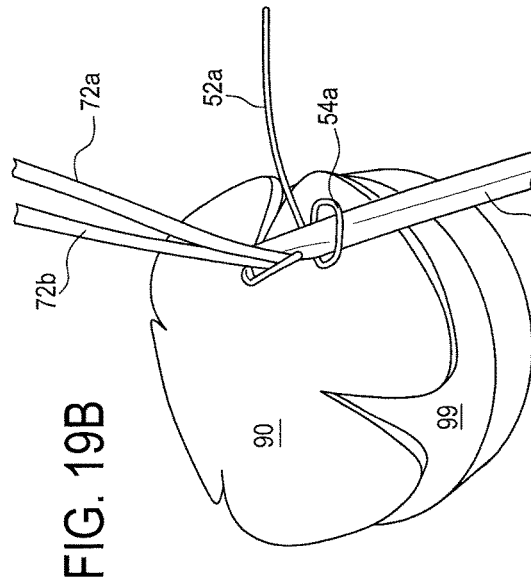
Figure 19C:
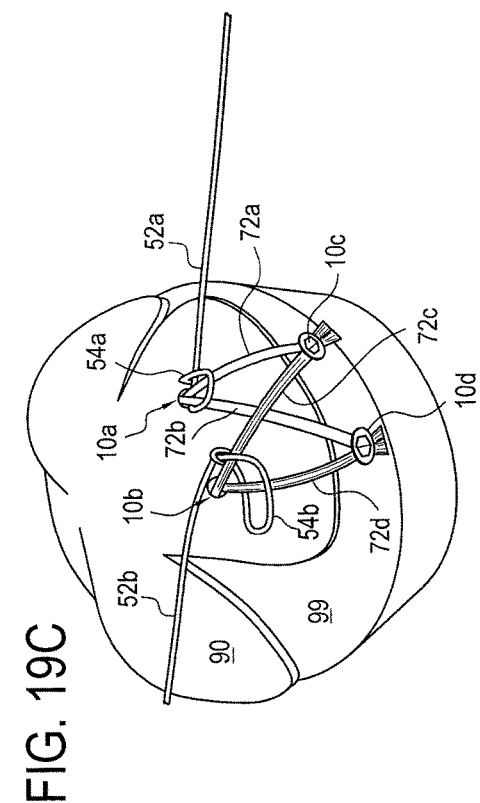
Figure 19D:
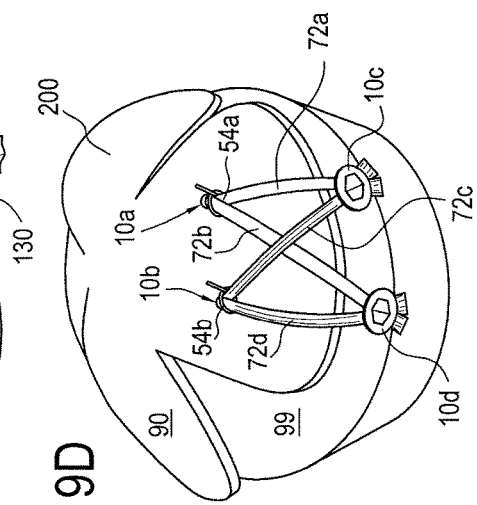

FIGS. 12-14 illustrate another example embodiment 30c of anchor tip 30. Anchor tip 30c can include eyelets 32c, hole 34c, and cannulated shaft 36c. Hole 34c is positioned at positioned at the proximal tip of anchor tip 30c. Cannulated shaft 36c can have an outer width 37c and an inner width 38c, where inner width 38c represents how wide the hollow portion of cannulated shaft 36c is. In an exemplary embodiment, hole 34c can be wider than the inner width 38c. In another exemplary embodiment, hole 34c and inner width 38c can be approximately the same width. In another exemplary embodiment, hole 34c can be narrower than inner width 38c. Additionally, tip body 31c can be wider than outer width 37c of cannulated shaft 36c. Proximal end 33c of anchor tip 30c can be wider than, about as wide as, or narrower than outer width 37c of cannulated shaft 36c. The size and shape of eyelets 32c can be any suitable size and shape. In the exemplary embodiment of FIGS. 12-14, eyelets 32c each have an approximately rectangular shape.

FIGS. 15-18 illustrate another exemplary embodiment 30d of anchor tip 30. Anchor tip 30d can include eyelet 32d, hole 34d, and cannulated shaft 36d. Hole 34d can be located on the side of anchor tip body 31d. Cannulated shaft 36d can have an outer width 37d and an inner width 38d, where inner width 38d represents how wide the hollow portion of cannulated shaft 36d is. Tip body 31d can be wider than outer width 37d of cannulated shaft 36d. Proximal end 33d of anchor tip 30d can be wider than, about as wide as, or narrower than outer width 37d of cannulated shaft 36d. The size and shape of eyelet 32d can be any suitable size and shape. In the exemplary embodiment of FIGS. 15-18, eyelet 32d has two rounded ends, wherein first rounded end 40d, located near proximal end 33d of anchor tip 30d, is smaller than second rounded end 41d located near cannulated shaft 36d.

FIGS. 19A-D illustrate simplified steps of an exemplary surgical tissue repair 100 with at least one exemplary fixation device described above. The exemplary surgical repair includes a medial row with first and second medial fixation devices 10a and 10b, and a lateral row with first and second lateral fixation devices 10c and 10d. First and second medial fixation devices 10a and 10b can be any embodiment of fixation device 10 described herein, and can comprise anchor body 20, anchor tip 30, tensionable construct 50, and flexible material 70.

First and second lateral fixation devices 10c and 10d can be any suitable knotless fixation devices known in the art. For example, first and second lateral fixation devices 10c and 10d can be any embodiment of fixation device 10 described herein, or any Arthrex SwiveLock® anchors (as disclosed and described in U.S. Pat. No. 8,012,174 issued Sep. 6, 2011, U.S. Pat. No. 9,005,246 issued Apr. 14, 2015, and U.S. 2013/0296936 published Nov. 7, 2013, the disclosures of all of which are fully incorporated by reference in their entirety herein) or any Arthrex PushLock™ anchors (as described in U.S. Pat. No. 7,329,272 issued Feb. 12, 2008, the disclosure of which is fully incorporated herein by reference), or any combination of these devices.

First and second lateral fixation devices 10c and 10d do not have a tensioning construct or suture construct pre-loaded. Instead, first and second lateral fixation devices 10c and 10d are secured to the surgical assembly by limbs 72a, 72b, 72c, and 72d of flexible materials 70a and 70b. A first limb 72a of flexible material 70a and a first limb 72c of flexible material 70b are passed through an eyelet (not pictured) of first lateral fixation device 10c before the eyelet is loaded into a prepared bone tunnel or hole. Tension can be adjusted if necessary prior to advancing anchor body (not pictured) of lateral fixation device 10c into the prepared bone tunnel or hole. A second limb 72b of flexible material 70a and a second limb 72d of flexible material 70b are similarly passed through an eyelet (not pictured) of second lateral fixation device 10d before the eyelet is loaded into a prepared bone tunnel or hole. Tension can be adjusted if necessary prior to advancing anchor body (not pictured) of lateral fixation device 10d into the prepared bone tunnel or hole. First and second limbs 72a and 72b of flexible material 70a pass through tensionable loop 54a and thus can be tensioned by pulling tensioning strand 52a. Similarly, first and second limbs 72c and 72d of flexible material 70b pass through tensionable loop 54b and can be tensioned by pulling tensioning strand 52b. Thus, the final surgical assembly of repair 100 (FIG. 19D) having four fixation devices is secured by flexible materials 70a and 70b, while tensioning constructs 50a and 50b provide additional tensioning capabilities in addition to providing a backup knotless repair separate from the repair by flexible materials 70a and 70b.

Methods of soft tissue repair utilizing the surgical assemblies and devices described above are also disclosed. FIGS. 20-30 illustrate more detailed steps of an exemplary embodiment of a tissue repair method to achieve final repair 200 (FIG. 30).

Figure 20:
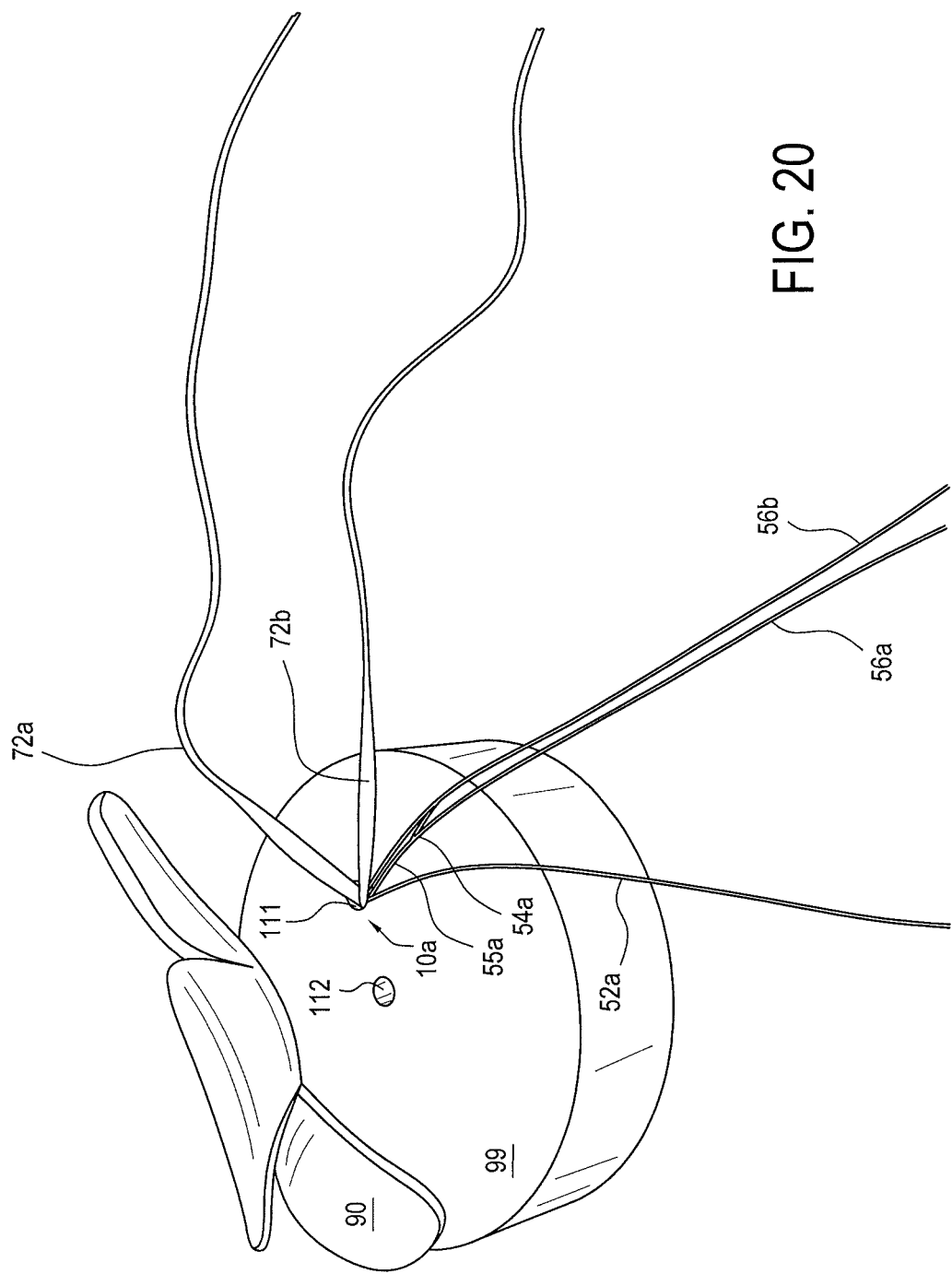
FIGS. 20-30 illustrate an exemplary method of tissue repair with the fixation device of FIG. 1.

FIG. 20 illustrates target tissue 90 and bone 99 with two prepared medial bone holes 111 and 112, with first tensionable knotless fixation device 10a implanted into prepared medial bone hole 111. Fixation device 10a has an anchor tip and anchor body (not visible since they have been implanted into prepared medial bone hole 111), tensionable construct 50a, and flexible material 70a. Tensionable construct has tensioning strand 52a, tensionable loop 54a, splice 55a, and loop strands 56a and 56b. Not pictured is the termination of the limbs into a single tensioning construct passing limb. Flexible material 70a has first limb 72a and second limb 72b. Not pictured is the termination of the limbs into a single flexible material passing limb. Tissue 90 may be soft tissue such as rotator cuff, for example.

Figure 21:
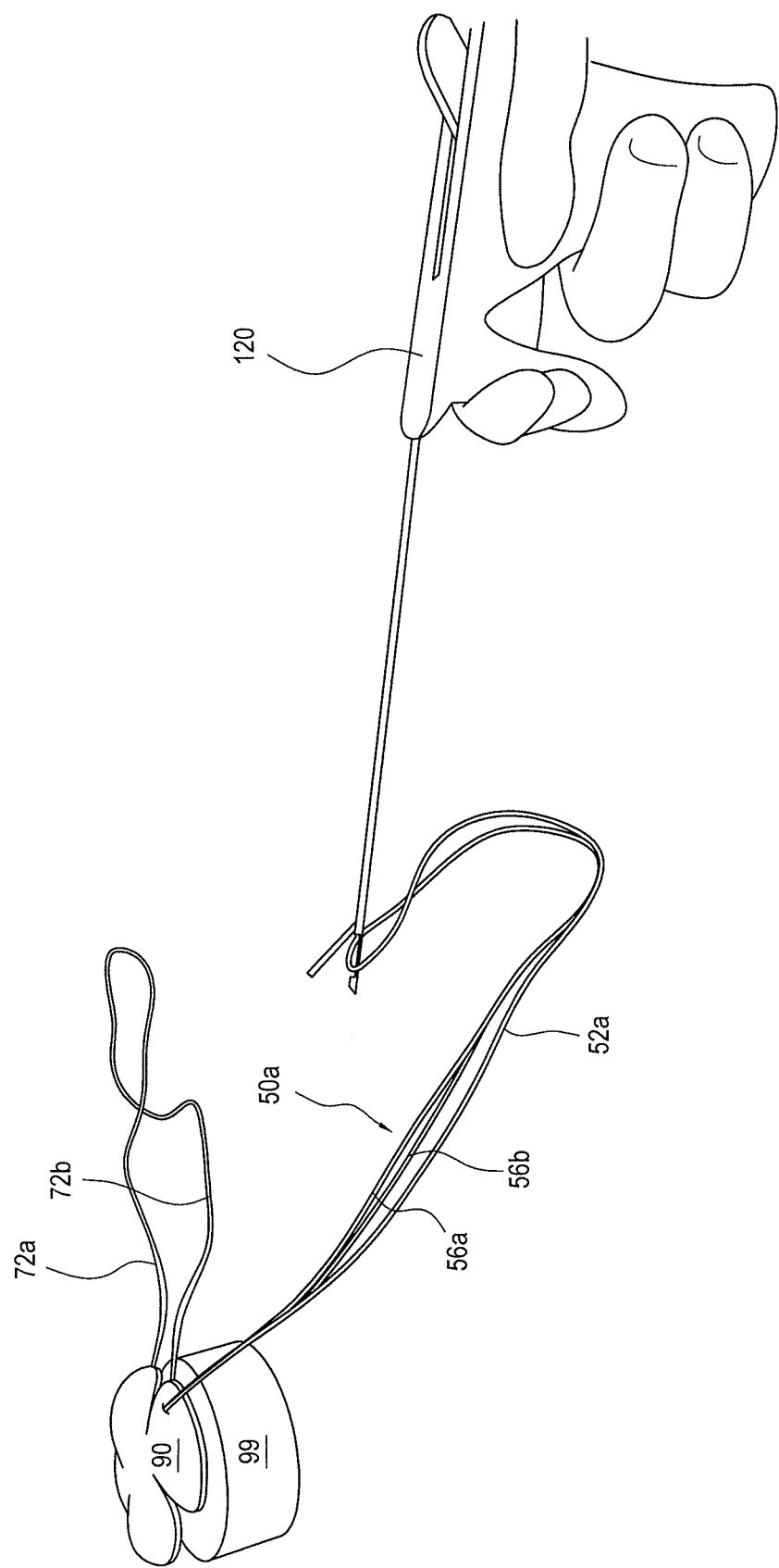

FIG. 21 illustrates the step of passing tensionable construct 50a through tissue 90 (for example, tendon, ligament, graft, etc.). In an exemplary embodiment, tensioning strand 52a and loop strands 56a and 56b terminate into a single tensioning construct passing limb 58a. Tensioning construct passing limb 58a is loaded into any suitable suture passer known in the art, for example the Arthrex Scorpion™ suture passer. Suture passer 120 is positioned in the desired location on the target tissue and tensioning construct passing limb 58a is passed through target tissue 90. In embodiments where tensioning strand 52a and loop strands 56a and 56b do not terminate into a single tensioning construct passing limb, then each strand may be passed separately, or loaded into a suture passer capable of passing multiple strands simultaneously.

Figure 22:
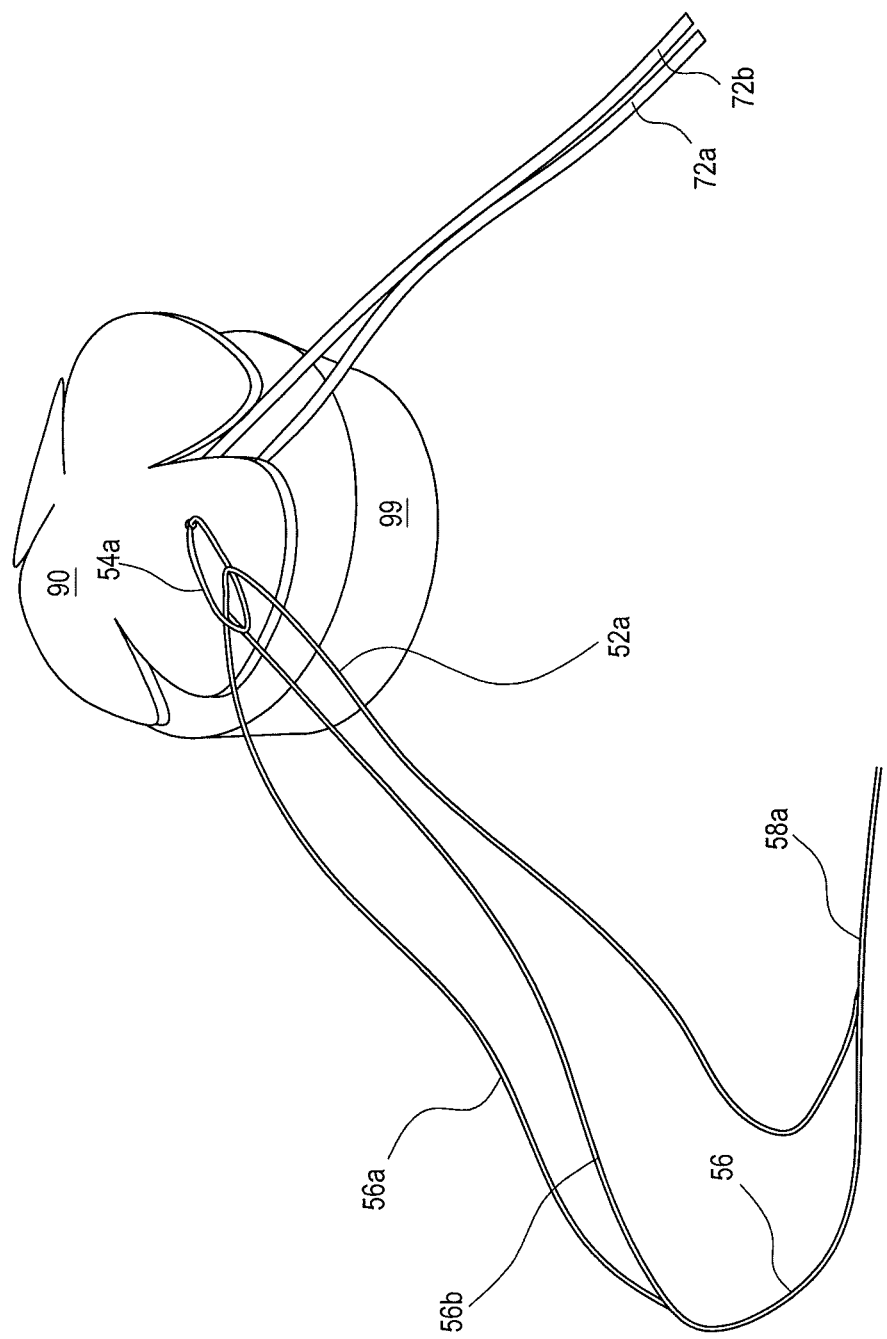

FIG. 22 illustrates tensioning construct passing limb 58a passed through target tissue 90. Tensioning construct passing limb 58a is pulled through target tissue such that tensioning strand 52a and tensionable loop 54a also pass through target tissue 90.

Figure 23:
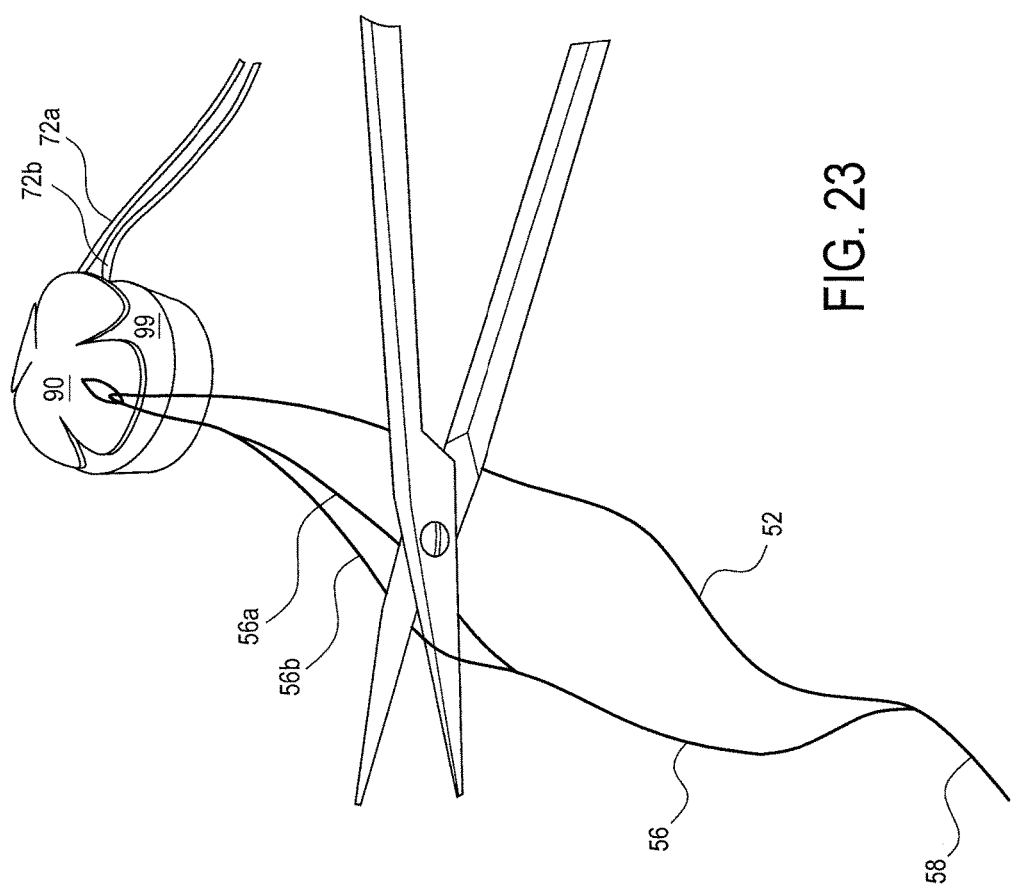
Figure 24:
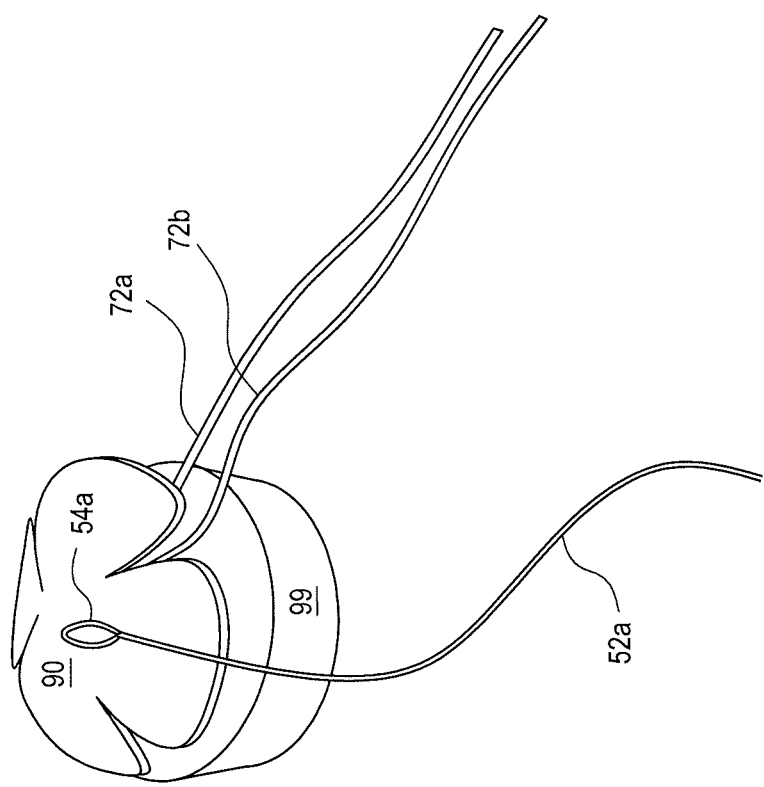

FIG. 23 illustrates the step of removing tensioning construct passing limb 58a from tensionable construct 50a. Cutting tensioning construct passing limb 58a leaves three strands: loop strands 56a, 56b, and tensioning strand 52a. Loop strands 56a and 56b wrap around tensionable loop 54a and may be discarded. FIG. 24 illustrates tensioning construct 50a with tensioning strand 52a and tensionable loop 54a passed through tissue 90, and loop strands 56a and 56b having been discarded. First and second limbs 72a and 72b of flexible material 70a have not yet been passed through tissue 90.

Figure 25:
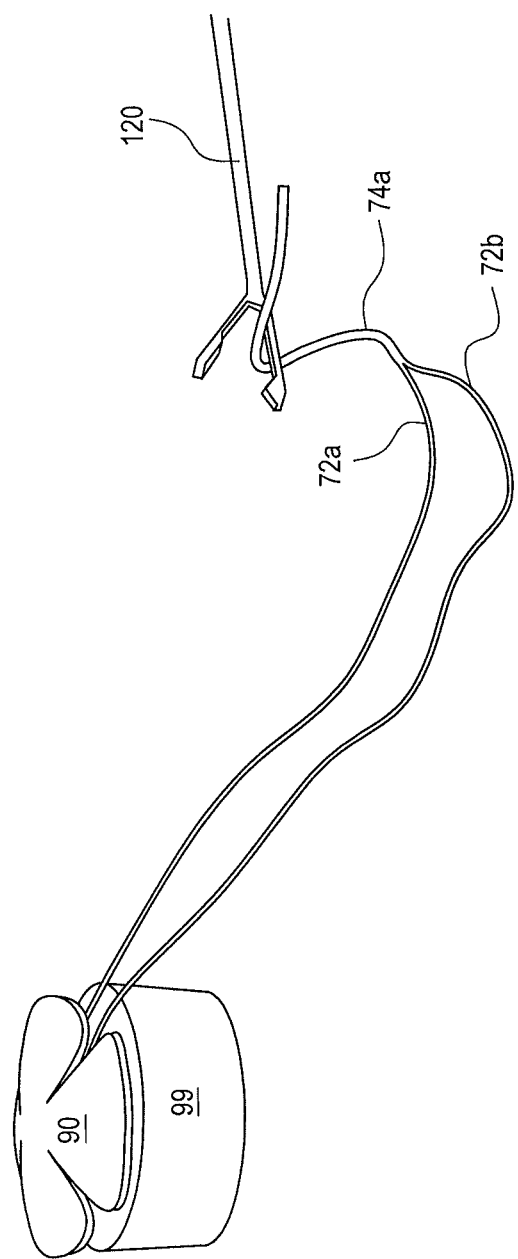

FIG. 25 illustrates the step of passing flexible material 70a through tissue 90. In an exemplary embodiment, first and second limbs 72a and 72b of flexible material 70a can terminate into a single flexible material passing limb 74a. Passing limb 74a is loaded into any suitable suture passer known in the art, for example the Arthrex Scorpion™ suture passer. Suture passer 120 is positioned at a location on the target tissue adjacent or near where tensioning construct 50a was passed, and passing limb 74a is passed through target tissue 90. In embodiments where first and second limbs 72a and 72b do not terminate into a passing limb, then each limb may be passed separately, or loaded into a suture passer capable of passing multiple limbs simultaneously.

Figure 26:
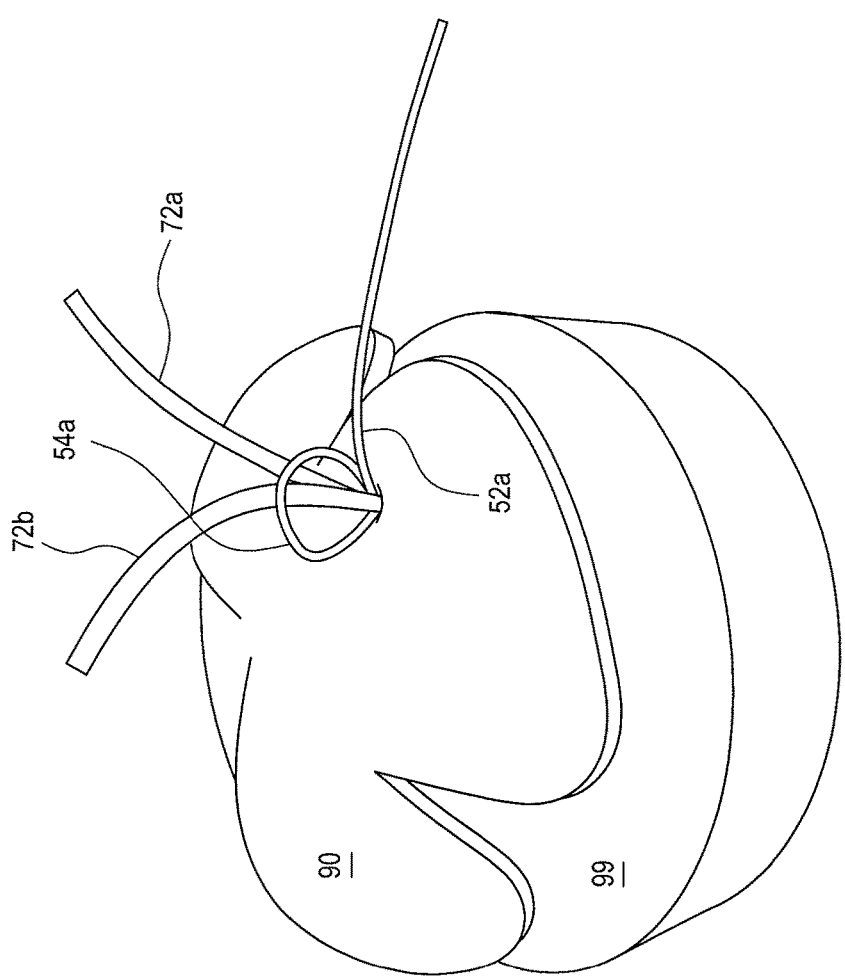

FIG. 26 illustrates tensioning strand 52a, tensionable loop 54a, and first and second limbs 72a and 72b all passed through tissue 90. Passing limb 74a has been cut and removed, leaving first and second limbs 72a and 72b separated.

Figure 27:
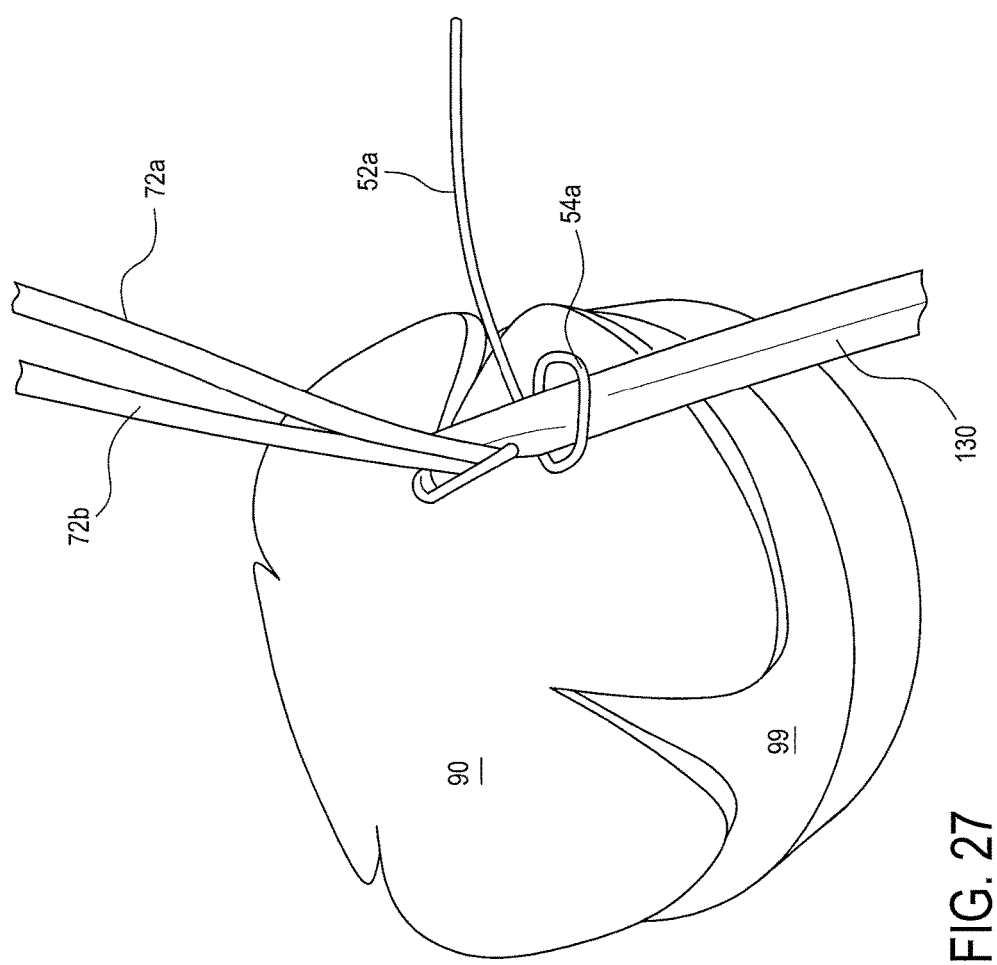

FIG. 27 illustrates the step of retrieving first and second limbs 72a and 72b through tensionable loop 54a. First and second limbs 72a and 72b can be retrieved using any retriever known in the art, for example the Arthrex Fiber-Tape® Retriever. After being loaded into retriever 130, limbs 72a and 72b are pulled through tensionable loop 54a.

Figure 28:
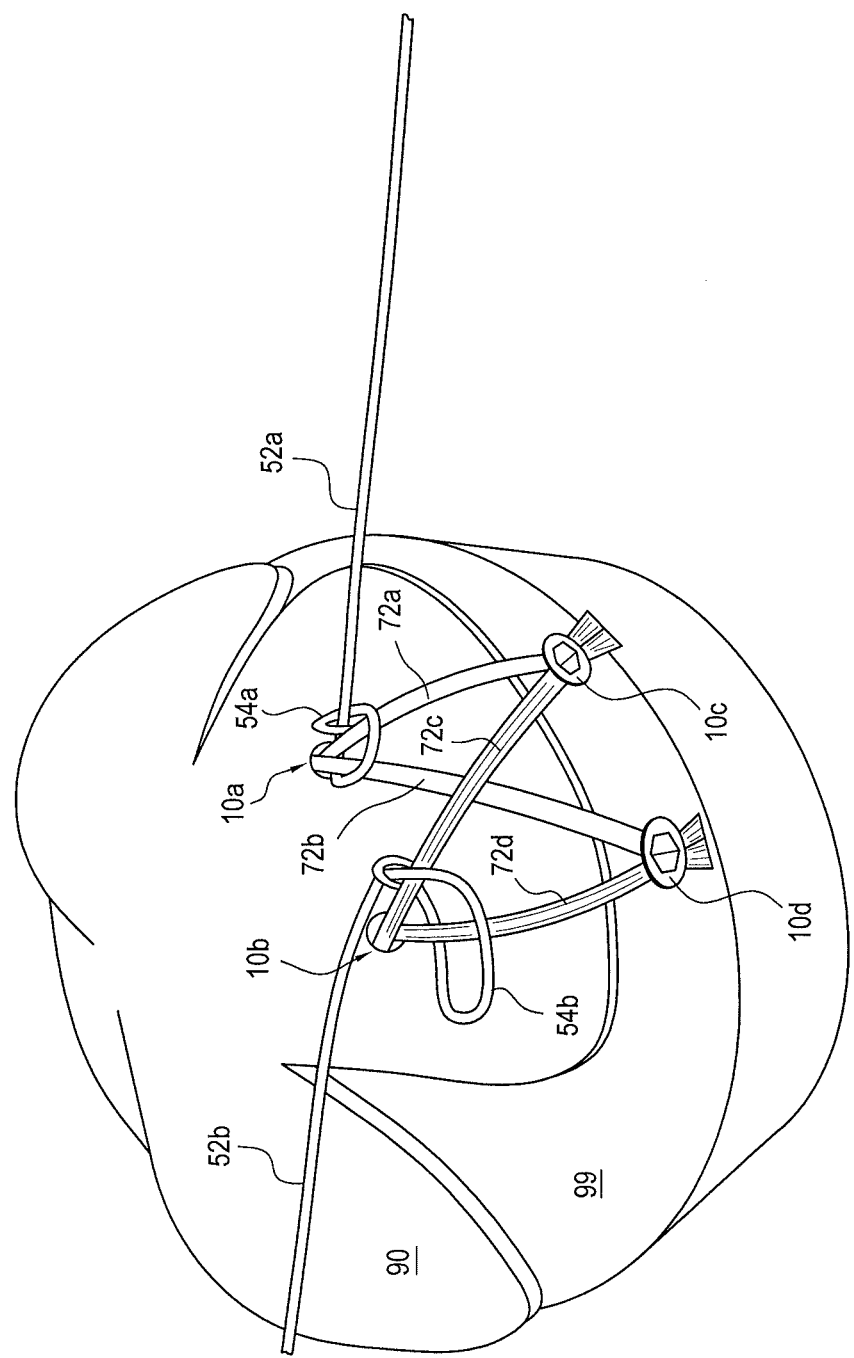

FIG. 28 illustrates the previously described steps having been repeated and completed for a second medial fixation device 10b. Second medial fixation device 10b has an anchor tip and anchor body (not visible since they have been implanted into prepared medial bone hole 112), tensionable construct 50b, and flexible material 70b. Tensionable construct has tensioning strand 52b, tensionable loop 54b, splice 55b, and loop strands (not pictured since they have already been discarded). Flexible material 70b has first limb 72c and second limb 72d.

Once first and second medial fixation devices 10a and 10b have been implanted, and tensioning strands 52a and 52b, tensionable loops 54a and 54b, splices 55a and 55b, and limbs 72a, 72b, 72c, and 72d have been passed through tissue 90, lateral bone holes can be prepared for first and second lateral fixation devices 10c and 10d. Lateral fixation devices 10c and 10d can be any suitable fixation devices, for example any embodiment of fixation device 10 described herein, or any Arthrex SwiveLock® anchors (as disclosed and described, for example, in U.S. Pat. No. 8,012,174 issued Sep. 6, 2011, U.S. Pat. No. 9,005,246 issued Apr. 14, 2015, and U.S. 2013/0296936 published Nov. 7, 2013, the disclosures of all of which are fully incorporated by reference in their entirety herein), or any Arthrex PushLock™ anchors (as described in U.S. Pat. No. 7,329,272 issued Feb. 12, 2008, the disclosure of which is fully incorporated herein by reference), or any screw-in or push-in type anchors, or any combination of these devices.

First and second lateral fixation devices 10c and 10d do not have a tensionable construct or flexible material (suture tape) pre-loaded. Instead, first and second lateral fixation devices 10c and 10d are secured to the surgical assembly by limbs 72a, 72b, 72c, and 72d of flexible material 70a and 70b. First limb 72a of flexible material 70a and a first limb 72c of flexible material 70b are passed through an eyelet (not pictured) of first lateral fixation device 10c before the eyelet is loaded into a prepared bone hole. Tension can be adjusted if necessary prior to advancing anchor body (not pictured) of lateral fixation device 10c into the prepared bone hole. Second limb 72b of flexible material 70a and a second limb 72d of flexible material 70b are similarly passed through an eyelet (not pictured) of the second lateral fixation device 10d before the eyelet is loaded into a prepared bone hole. Tension can be adjusted if necessary prior to advancing anchor body (not pictured) of lateral fixation device 10d into the prepared bone hole.

After first and second lateral fixation devices 10c and 10d have been fixated/inserted/implanted, the resulting surgical assembly is shown in FIG. 28. Any remainder of limbs 72a, 72b, 72c, and 72d extending out from lateral fixation devices

10c and 10d may be cut off using any suitable suture cutter, for example the Arthrex FiberWire® cutter. FIG. 28 also illustrates the step of pulling tensioning strand 52a to tighten tensionable loop 54a in order to apply tension to first and second limbs 72a and 72b.

Figure 29:
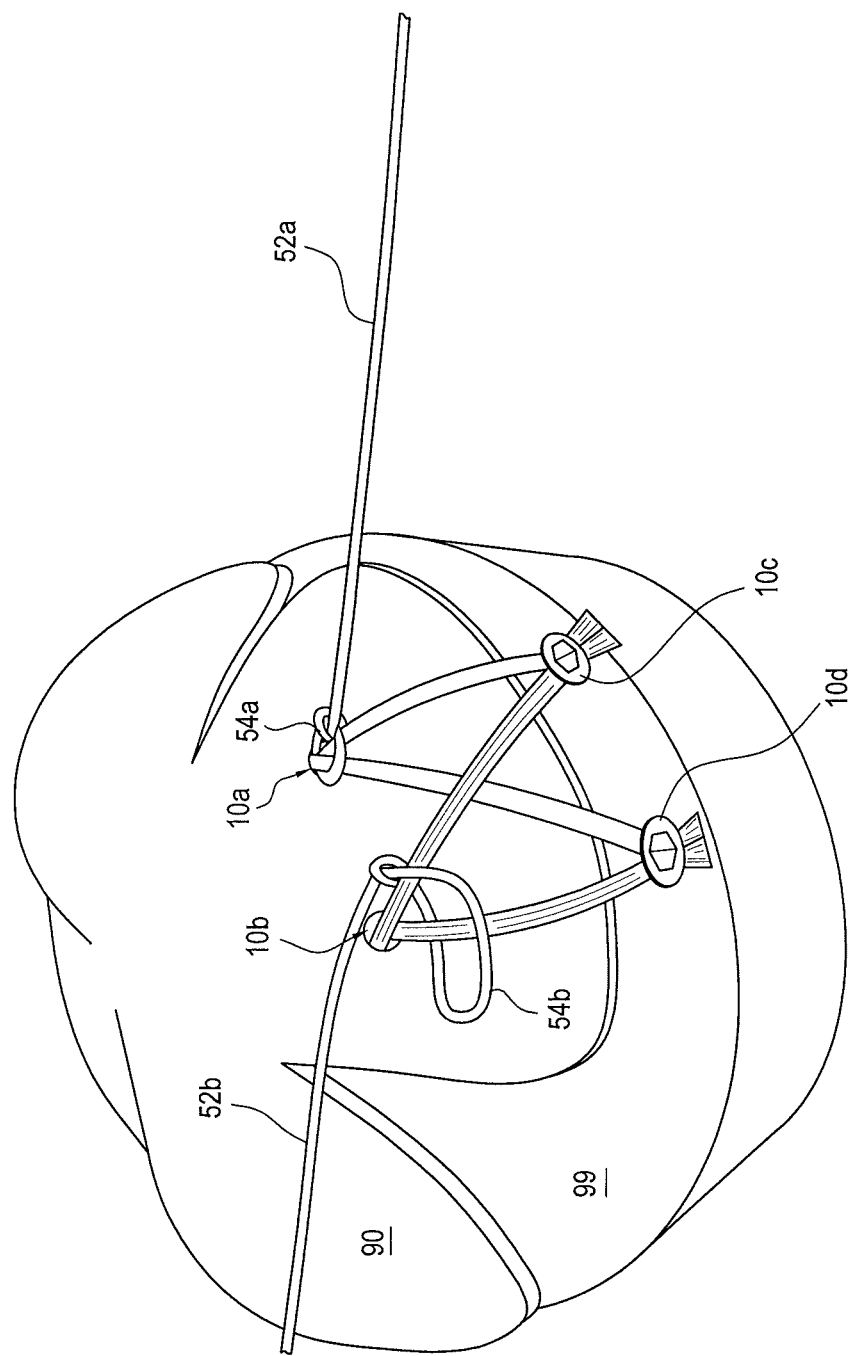
Figure 30:
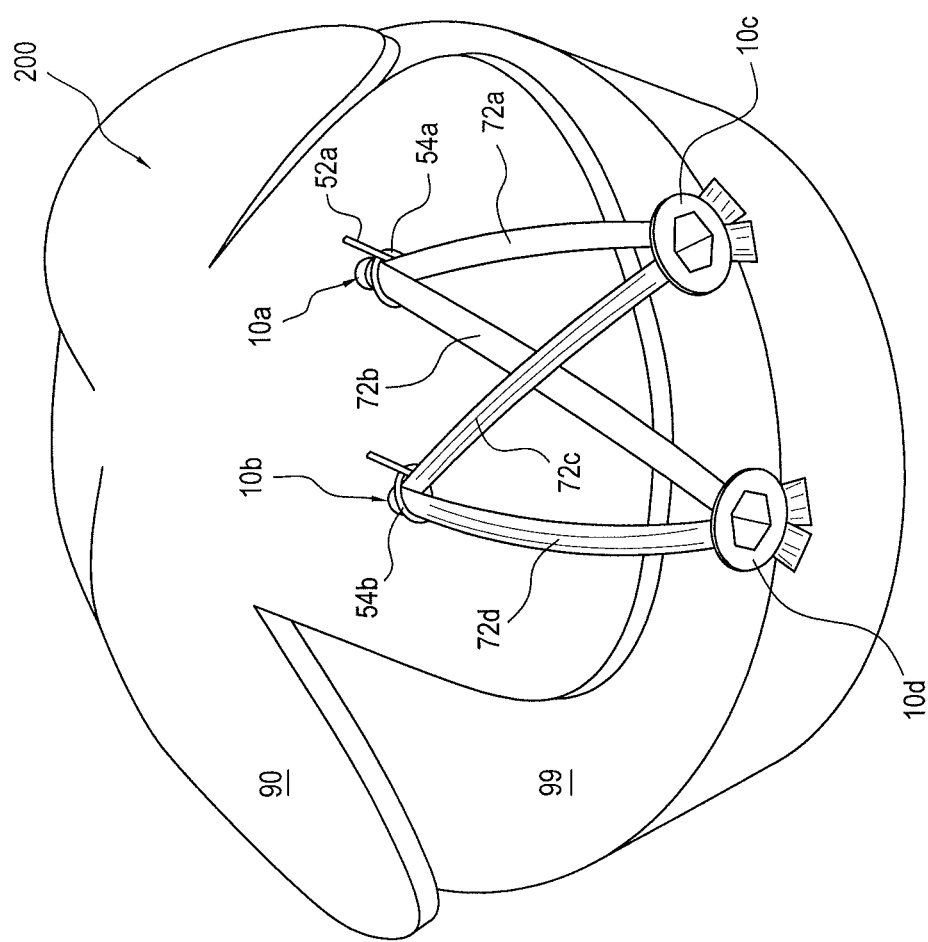

FIG. 29 illustrates the step of pulling tensioning strand 52b to tighten tensionable loop 54b in order to apply tension to first and second limbs 72c and 72d of suture construct 70b.

FIG. 30 illustrates the final surgical repair 200. Tensionable loops 54a and 54b have been tensioned, and tensioning strands 52a and 52b have been cut to remove them from the final assembly. Tensioning strands 52a and 52b can be cut using any suitable suture cutter, for example the Arthrex FiberWire® cutter.

An exemplary method of tissue repair comprises inter alia the steps of: (i) inserting into bone a surgical assembly comprising a fixation device; a tensionable construct pre-loaded on the fixation device, the tensionable construct including a tensioning strand, a knotless, adjustable, self-cinching, tensionable loop having an adjustable perimeter, and a splice adjacent the loop; and a flexible material (for example, suture tape) attached to the fixation device; and (ii) passing the tensionable construct and limbs of the flexible material around or through tissue to be fixated (or reattached) to bone, so that the tensionable loop is positioned over the tissue, and then passing limbs of the flexible material through the tensionable loop. The method may further comprise the step of securing the limbs of the flexible material into bone. The limbs may be secured with at least another fixation device that is inserted into bone. The method may further comprise the step of pulling on the tensioning strand to appropriate tissue to bone. The tissue may be soft tissue such as tendon, ligament, or graft.

Another exemplary method of soft tissue repair comprises inter alia the steps of: (i) inserting into bone a surgical assembly comprising a fixation device; a tensionable construct pre-loaded on the fixation device, the tensionable construct including a tensioning strand, a knotless, adjustable, self-cinching, tensionable loop having an adjustable perimeter, and a splice adjacent the loop; and a flexible material (for example, suture tape) attached to the fixation device; (ii) passing the tensionable construct and limbs of the flexible material around or through tissue to be fixated (or reattached) to bone so that the tensionable loop is positioned above and over the soft tissue, and above and over the bone; (iii) subsequently, passing limbs of the flexible material through the tensionable loop; and (iv) passing the limbs of the flexible material over the tissue and securing the limbs with additional fixation devices into bone, to form a mattress stich repair.

Another exemplary method of soft tissue repair comprises inter alia the steps of: (i) inserting into bone a plurality of surgical assemblies, each surgical assembly comprising a fixation device; a tensionable construct pre-loaded on the fixation device, the tensionable construct including a tensioning strand, a knotless, adjustable, self-cinching, closed, tensionable loop having an adjustable perimeter, and a splice adjacent the loop; and a flexible material (for example, suture or suture tape) attached to the fixation device; (ii) passing the tensionable construct and limbs of the flexible material—of each surgical assembly—around or through tissue to be fixated (or reattached) to bone, so that the tensionable loop of each surgical assembly is positioned over and above the soft tissue, and over and above the bone; (iii) subsequently, passing limbs of the flexible material of each surgical assembly through the corresponding tensionable loop; and (iv) passing the limbs of each surgical assembly over the tissue, and securing the limbs with a plurality of fixation devices into bone, to form a mattress stich repair.

The flexible strands and materials described above may be formed of strands of high strength suture material with surgically-useful qualities, including knot tie down characteristics and handling, such as Arthrex FiberWire® suture disclosed in U.S. Pat. No. 6,716,234, the disclosure of which is incorporated by reference in its entirety herein. FiberWire® suture is formed of an advanced, high-strength fiber material, namely ultrahigh molecular weight polyethylene (UHMWPE), sold under the tradenames Spectra (Honeywell) and Dyneema (DSM) fibers, braided with at least one other fiber, natural or synthetic, to form lengths of suture material. The flexible strand may be a high-strength suture, such as an ultrahigh molecular weight polyethylene (UHMWPE) suture which is the preferred material as this material allows easy splicing.

The suture constructs may be formed of optional colored strands, such as black or blue, to assist surgeons in distinguishing between suture lengths with the trace and suture lengths without the trace. Preferably, each of the limbs may be provided in different colors to assist surgeons in retrieving one limb from each of the knotless fixation devices and then loading them through another knotless fixation device, during the formation of the criss-cross suturing pattern.

Suture constructs may be coated (partially or totally) with wax (beeswax, petroleum wax, polyethylene wax, or others), silicone, silicone rubbers, PTFE (Teflon, Hostaflon, or others), PBA (polybutylate acid), ethyl cellulose (Filodel) or other coatings, to improve lubricity of the suture or tape, knot security, pliability, handleability, or abrasion resistance, for example.

Suture constructs may also contain a bioabsorbable material, such as PLLA or one of the other polylactides, for example, and/or may be formed of twisted fibers having strands of a contrasting color added to the braided threads, to make the suture more visible during surgical procedures. The colored strands can be dyed filaments or strands, for example.

The surgical assembly and methods of the present invention have applicability to tissue repairs such as rotator cuff repair, Achilles tendon repair, patellar tendon repair, knee repairs such as ACL and/or PCL reconstruction, hip and shoulder reconstruction procedures, and applications involving repairing soft tissue to bone.

What is claimed is:

1. A surgical assembly for tissue repair, comprising:
   a fixation device comprising:
   (i) an anchor tip; and
   (ii) a cannulated anchor body, separate from the anchor tip, and insertable over the anchor tip by advancing the anchor body over the anchor tip, the anchor body having a fixation exterior for securing the fixation device in a bone hole;
   a tensionable construct pre-loaded onto the fixation device and coupled to the anchor tip, wherein the tensionable construct comprises a flexible strand with a free end and a knot, a splice, and a knotless, adjustable, tensionable, self-cinching loop formed adjacent the splice and having an adjustable perimeter; and
   a flexible material threaded through the anchor tip of the fixation device.

2. The surgical assembly of claim 1, wherein the anchor tip is rotatably attached to the anchor body such that the anchor tip is rotatable with respect to the anchorbody.

3. The surgical assembly of claim 1, wherein the anchor tip is rotatably received within the anchor body upon advancement of the anchor body over a shaft of the anchor tip, the anchor tip being configured to receive the tensionable construct and the flexible material.

4. The surgical assembly of claim 1, wherein the tensionable construct consists of a flexible strand with a knot and a free end, a splice, and a knotless, adjustable, tensionable, self-cinching, closed loop formed adjacent the splice.

5. The surgical assembly of claim 1, wherein the flexible material consists of one or more suture tapes.

6. The surgical assembly of claim 1, wherein the flexible material is releasably attached to an eyelet of the anchor tip.

7. The surgical assembly of claim 1, wherein the flexible material comprises a first limb and a second limb, the first and second limbs terminating into a suture construct passing limb.

8. The surgical assembly of claim 1, wherein the flexible material is fixedly attached to an eyelet of the anchor tip.

9. A surgical assembly for tissue repair, comprising:
   a fixation device comprising:
      (i) an anchor tip comprising a cannulated shaft attached to an anchor tip body, the anchor tip body including an eyelet and a passage; and
      (ii) a cannulated anchor body, separate from the anchor tip, and insertable over the anchor tip by advancing the anchor body over the anchor tip, the anchor body having a fixation exterior for securing the fixation device in a bone hole;
   a tensionable construct pre-loaded onto the fixation device and coupled to the anchor tip; and
   a flexible material threaded through the eyelet of the anchor tip.

10. The surgical assembly of claim 9, wherein the tensionable construct comprises a flexible strand with a free end and a knot, a splice, and a knotless, adjustable, tensionable, self-cinching loop formed adjacent the splice and having an adjustable perimeter.

11. The surgical assembly of claim 9, wherein the tensionable construct extends through the passage, and through at least a portion of the anchor body of the fixation device.

12. The surgical assembly of claim 9, wherein the tensionable construct passes through the cannulated shaft of the anchor tip and through the anchor body.

13. The surgical assembly of claim 9, wherein the passage extends in a direction about perpendicular to a longitudinal axis of the eyelet.

14. A surgical assembly for tissue repair, comprising:
   a fixation device comprising:
      (i) a swivel anchor tip comprising an eyelet and a hole;
      (ii) a cannulated anchor body, separate from the swivel anchor tip, and insertable over the swivel anchor tip by rotatable advancement of the anchor body relative to the swivel anchor tip, the cannulated anchor body having a fixation exterior for securing the fixation device in a bone hole;
   a tensionable construct pre-loaded onto the fixation device and passing through the hole of the swivel anchor tip; and
   a flexible material attached to the fixation device and passing through the eyelet of the swivel anchor tip.

15. The surgical assembly of claim 14, wherein the flexible material comprises at least one of a flexible strand, a suture, or tape.

16. The surgical assembly of claim 14, wherein the swivel anchor tip comprises a cannulated shaft.

17. The surgical assembly of claim 16, wherein the hole is wider than an inner width of the cannulated shaft.

18. The surgical assembly of claim 14, wherein the eyelet has a first orientation and the hole has a second orientation that is different than the first orientation.

19. The surgical assembly of claim 18, wherein the hole extends in a direction about perpendicular to a longitudinal axis of the eyelet.

20. The surgical assembly of claim 14, wherein the tensionable construct comprises a flexible strand with a free end and a knot, a splice, and a knotless, adjustable, tensionable, self-cinching loop formed adjacent the splice and having an adjustable perimeter.

21. The surgical assembly of claim 14, wherein the exterior of the anchor body includes threads or ridges.

* * * * *